US012622636B2

(12) United States Patent
Akamatsu et al.

(10) Patent No.: US 12,622,636 B2
(45) Date of Patent: *May 12, 2026

(54) BODY FLUID VOLUME ESTIMATION DEVICE, BODY FLUID VOLUME ESTIMATION METHOD, AND NON-TRANSITORY COMPUTER-READABLE MEDIUM

(71) Applicant: NEC Corporation, Tokyo (JP)

(72) Inventors: Yusuke Akamatsu, Tokyo (JP); Yoshifumi Onishi, Tokyo (JP); Hideo Tsurushima, Ibaraki (JP)

(73) Assignee: NEC CORPORATION, Tokyo (JP)

( * ) Notice: Subject to any disclaimer, the term of this patent is extended or adjusted under 35 U.S.C. 154(b) by 267 days.

This patent is subject to a terminal disclaimer.

(21) Appl. No.: 18/216,806

(22) Filed: Jun. 30, 2023

(65) Prior Publication Data

US 2024/0008803 A1     Jan. 11, 2024

(30) Foreign Application Priority Data

Jul. 7, 2022     (JP) ................................. 2022-109664

(51) Int. Cl.
*A61B 5/00* (2006.01)
*A61B 5/107* (2006.01)
(52) U.S. Cl.
CPC ............ *A61B 5/443* (2013.01); *A61B 5/1079* (2013.01)
(58) Field of Classification Search
CPC ................................ A61B 5/443; A61B 5/1079
See application file for complete search history.

(56) References Cited

U.S. PATENT DOCUMENTS

2017/0112429 A1     4/2017  Matsuda
2018/0144465 A1     5/2018  Hsieh et al.
(Continued)

FOREIGN PATENT DOCUMENTS

JP          2005-065812 A       3/2005
JP          2020-500378 A       1/2020
(Continued)

OTHER PUBLICATIONS

J. Chen et.al, "Camera-Based Peripheral Edema Measurement Using Machine Learning," in Proc. IEEE Int. Conf. Healthcare Informatics (ICHI), 2018, pp. 115-122.
(Continued)

*Primary Examiner* — Ming Shui
(74) *Attorney, Agent, or Firm* — Sughrue Mion, PLLC

(57) ABSTRACT

A body fluid volume estimation device includes a pre-training unit, a transfer learning unit, and an estimation unit. The pre-training unit performs pre-training by using, as supervised information, information indicating body fluid volumes of the multiple patients when face images of multiple patients are captured. The transfer learning unit further performs transfer learning on multiple face images of one specific patient after the pre-training, and constructs a trained model. The estimation unit estimates, by inputting a face image of the one specific patient to the trained model, a body fluid volume at a point in time at which the face image of the one specific patient is captured. By estimating a body fluid volume from a face image by machine learning, the body fluid volume can be used for assistance such as decision making of a user.

11 Claims, 13 Drawing Sheets

(56)     References Cited

U.S. PATENT DOCUMENTS

| | | | |
|---|---|---|---|
| 2019/0029592 A1* | 1/2019 | Yao ........................ | A61B 5/443 |
| 2019/0220975 A1 | 7/2019 | Hsieh et al. | |
| 2020/0060613 A1 | 2/2020 | Lee et al. | |
| 2020/0170564 A1 | 6/2020 | Jiang et al. | |
| 2022/0319676 A1* | 10/2022 | Bosanac .............. | G06N 3/0464 |

FOREIGN PATENT DOCUMENTS

| | | |
|---|---|---|
| JP | 2020-199072 A | 12/2020 |
| JP | 2022-512044 A | 2/2022 |
| WO | 2015/166692 A1 | 11/2015 |

OTHER PUBLICATIONS

A. G. Smith et.al, "Objective determination of peripheral edema in heart failure patients using short-wave infrared molecular chemical imaging," Journal of Biomedical Optics, vol. 26, No. 10, pp. 105002, 2021.

Kaiming He et al., "Momentum Contrast for Unsupervised Visual Representation Learning", in Proc. IEEE/CVF conf. computer vision and pattern recognition (CVPR), 2020, pp. 9729-9738.

T. Chen, S. Kornblith, M. Norouzi, and G. Hinton, "A simple framework for contrastive learning of visual representations," Proc. Int. conf. machine learning (ICML), 2020, pp. 1597-1607.

P. Khosla et al., "Supervised Contrastive Learning", in Proc. Advances in Neural Information Processing Systems (NeurIPS), vol. 33, pp. 18661-18673, 2020.

B. Dufumier et al., "Contrastive Learning with Continuous Proxy Meta-Data for 3D MRI Classification", in Int. Conf. Medical Image Computing and Computer-Assisted Intervention (MICCAI), 2021, pp. 58-68.

D. P. Kingma and J. Ba, "Adam: a Method for Stochastic Optimization," arXiv preprint arXiv: 1412.6980, 2014.

J. Deng, W. Dong, R. Socher, L. Li, et al., "Imagenet: A Large-Scale Hierarchical Image Database," Proc. IEEE/CVF conf. computer vision and pattern recognition (CVPR), 2009, pp. 248-255.

JP Official Communication for JP Application No. 2022-109664, mailed on Mar. 3, 2026 with English Translation.

Tomohiko Naruse, Yuzo Watanabe, XII Abnormal blood pressure, "Abnormal blood pressure in dialysis patients," Extra issue Nippon Rinsho, Syndrome by region Series No. 8, Circulatory System Syndrome (The 3rd Edition) (IV)—Including cardiovascular disease-, vol. 8, The 3rd Edition, Japan, Nipponrinshosha Co., Ltd., Mar. 31, 2020, pp. 100-104.

* cited by examiner

| | | CLASSIFICATION ESTIMATION BEFORE AND AFTER DIALYSIS | | | WEIGHT PREDICTION | | |
| | | Accuracy | ROC-AUC | PR-AUC | MAE | RMSE | CorrCoef |
|---|---|---|---|---|---|---|---|
| | FIRST COMPARATIVE EXAMPLE WITHOUT ADVANCE LEARNING | 69.8±9.7 | 77.3±11.9 | 78.3±11.1 | 0.766±0.126 | 0.892±0.129 | 0.401±0.235 |
| SELF-SUPERVISED LEARNING | SECOND COMPARATIVE EXAMPLE SimCLR | 75.3±8.8 | 84.5±9.4 | 84.7±8.8 | 0.661±0.130 | 0.789±0.137 | 0.557±0.176 |
| | THIRD COMPARATIVE EXAMPLE MoCo | 77.2±9.2 | 86.3±10.0 | 87.5±9.0 | 0.620±0.128 | 0.735±0.134 | 0.610±0.170 |
| | FOURTH COMPARATIVE EXAMPLE Cross Entropy | 80.2±7.8 | 88.1±7.5 | 88.7±6.5 | 0.591±0.109 | 0.700±0.110 | 0.664±0.122 |
| SUPERVISED LEARNING | FIFTH COMPARATIVE EXAMPLE SupCon | 77.7±9.4 | 86.6±10.4 | 90.0±9.6 | 0.636±0.118 | 0.743±0.121 | 0.603±0.151 |
| | SIXTH COMPARATIVE EXAMPLE y-Aware InfoNCE | 82.7±7.2 | 91.7±7.0 | 92.2±7.0 | 0.547±0.134 | 0.648±0.134 | 0.697±0.139 |
| | WeightSupMoCo | 84.9±7.1 | 92.5±7.6 | 93.0±7.2 | 0.526±0.135 | 0.626±0.137 | 0.719±0.136 |

Fig. 8

BODY FLUID VOLUME ESTIMATION DEVICE, BODY FLUID VOLUME ESTIMATION METHOD, AND NON-TRANSITORY COMPUTER-READABLE MEDIUM

INCORPORATION BY REFERENCE

This application is based upon and claims the benefit of priority from Japanese patent application No. 2022-109664, filed on Jul. 7, 2022, the disclosure of which is incorporated herein in its entirety by reference.

TECHNICAL FIELD

The present disclosure relates to a body fluid volume estimation device, a body fluid volume estimation method, and a non-transitory computer-readable medium.

BACKGROUND ART

In recent years, development of a technique for determining a health state of a person and presence or absence of a disease from an appearance of the person, for example, an image of a face and the like has been progressing (Published Japanese Translation of PCT International Publication for Patent Application, No. 2022-512044, Japanese Unexamined Patent Application Publication No. 2020-199072, and Japanese Unexamined Patent Application Publication No. 2005-65812). In general, it is known that a change occurs in a form of a face and a lower limb according to a health state of a person. An increase in capacity of a body is detected as a swelling, and a decrease in capacity is detected as a decrease in firmness of skin. A swelling mainly refers to a state where excessive water is accumulated in a gap of tissue and a body fluid volume increases, and occurs by various causes such as a central disease, a respiratory/circulatory disease, a renal disease, an orthopedic disease, a metabolic disease, and a malignant tumor. Further, a decrease in firmness of skin occurs by a decrease in water in a body, and occurs in various states such as dehydration and heatstroke.

For example, a swelling occurs when a waste matter and water in a body cannot be removed due to a decrease in renal function, and thus excessive water in a body is removed by dialysis treatment in a present condition. Therefore, it is important for a dialysis patient to maintain water in a body (i.e., a body fluid volume) within a desirable range, and thus an intake of water and salt needs to be limited in daily life.

As a change in weight, factors such as a change in body fluid volume, fat mass, and muscle mass are conceivable. Since it is conceivable that dialysis is performed for approximately four hours, and a change in fat mass and muscle mass does not occur during the dialysis, a change in weight by the dialysis conceivably reflects a change in body fluid volume. Further, for elderly patients having a chronic heart failure, it is also inconceivable that muscle mass is increased by exercise and an increase in amount of food leads to an increase in fat, and thus a change in weight may conceivably represent a change in body fluid volume. Furthermore, also in dehydration, fat mass and muscle mass do not change in a short period of time, and thus a change in weight may conceivably represent a change in body fluid volume.

In order to recognize a state of a patient having a disease accompanied by a swelling, a degree of the swelling of the patient, i.e., a body fluid volume is required to be measured. As a general swelling estimation technique, for example, a technique of measuring a degree of a swelling by a pitting test by a medical staff member has been proposed (J. Chen et. al, "Camera-Based Peripheral Edema Measurement Using Machine Learning," in Proc. IEEE Int. Conf. Healthcare Informatics (ICHI), 2018, pp. 115-122.) In this technique, an image is captured during a pitting test of a lower limb, and a degree of a peripheral swelling of a lower limb or the like is estimated from the image by support vector machine (SVM) or a convolutional neural network (CNN).

Further, a technique (A. G. Smith et. al, "Objective determination of peripheral edema in heart failure patients using short-wave infrared molecular chemical imaging," Journal of Biomedical Optics, vol. 26, No. 10, pp. 105002, 2021) of measuring a degree of a swelling, based on an image in which a peripheral portion such as hands and feet of a patient is captured, by using a short-wave infrared (SWIR) camera has been proposed. In this technique, by using a property in which an absorption coefficient of water, collagen, and fat increases in a specific spectrum region of the SWIR camera in presence of a swelling, a swelling level can be estimated from a spectrum component.

SUMMARY

As described above, in order to manage a degree of a swelling of a patient, i.e., a body fluid volume on a daily basis, it is desirable that the patient himself/herself measures a body fluid volume, and manages an intake of water according to a measurement result. However, the technique for measuring a body fluid volume described above needs to be performed by a professional medical staff member, and there is also a restriction that specific equipment such as a special camera is needed.

Meanwhile, in order for a patient to autonomously limit an intake of water and salt in daily life, a technique for a patient to be able to measure a body fluid volume on a daily basis is required to be established.

The present disclosure has been made in view of the circumstances described above, and an example object of the invention is to estimate a body fluid volume of a patient from a face image of the patient.

In a first example aspect of the present disclosure, a body fluid volume estimation device includes: a pre-training unit configured to perform pre-training on face images of multiple patients by using, as supervised information, information indicating a body fluid volume of each of the plurality of patients when the face images of the plurality of patients are captured; a transfer learning unit configured to further perform transfer learning on multiple face images of one specific patient after the pre-training, and construct a trained model; and an estimation unit configured to estimate, by inputting a face image of the one specific patient to the trained model, a body fluid volume of the one specific patient at a point in time at which the face image of the one specific patient is captured.

In a second example aspect of the present disclosure, a body fluid volume estimation method includes: performing pre-training on face images of multiple patients by using, as supervised information, information indicating a body fluid volume of each of the plurality of patients when the face images of the plurality of patients are captured; further performing transfer learning on multiple face images of one specific patient after the pre-training, and constructing a trained model; and estimating, by inputting a face image of the one specific patient to the trained model, a body fluid volume of the one specific patient at a point in time at which the face image of the one specific patient is captured.

In a third example aspect of the present disclosure, a non-transitory computer-readable medium storing a program causing a computer to execute: processing of performing pre-training on face images of multiple patients by using, as supervised information, information indicating a body fluid volume of each of the plurality of patients when the face images of the plurality of patients are captured; processing of further performing transfer learning on multiple face images of one specific patient after the pre-training, and constructing a trained model; and processing of estimating, by inputting a face image of the one specific patient to the trained model, a body fluid volume of the one specific patient at a point in time at which the face image of the one specific patient is captured.

The present disclosure is able to estimate a body fluid volume of a patient from a face image of the patient.

BRIEF DESCRIPTION OF DRAWINGS

The above and other aspects, features and advantages of the present disclosure will become more apparent from the following description of certain exemplary embodiments when taken in conjunction with the accompanying drawings, in which:

FIG. 8 is a diagram illustrating estimation performance of classification before and after dialysis and weight prediction in each technique;

EXAMPLE EMBODIMENT

Example embodiments of the present disclosure will be described below with reference to the drawings. In each of the drawings, the same elements will be denoted by the same reference signs, and duplicate description will be omitted as necessary.

First Example Embodiment

A body fluid volume estimation device 100 according to a first example embodiment will be described. The body fluid volume estimation device 100 is configured to perform contrastive learning by weight-aware supervised momentum contrast (WeightSupMoCo) being a new technique on a face image of a patient, based on information representing a body fluid volume of the patient. Then, the body fluid volume estimation device 100 can estimate a body fluid volume of a patient being an estimation target, for example, a change in the body fluid volume by inputting a face image of the patient to a trained model.

Figure 1:
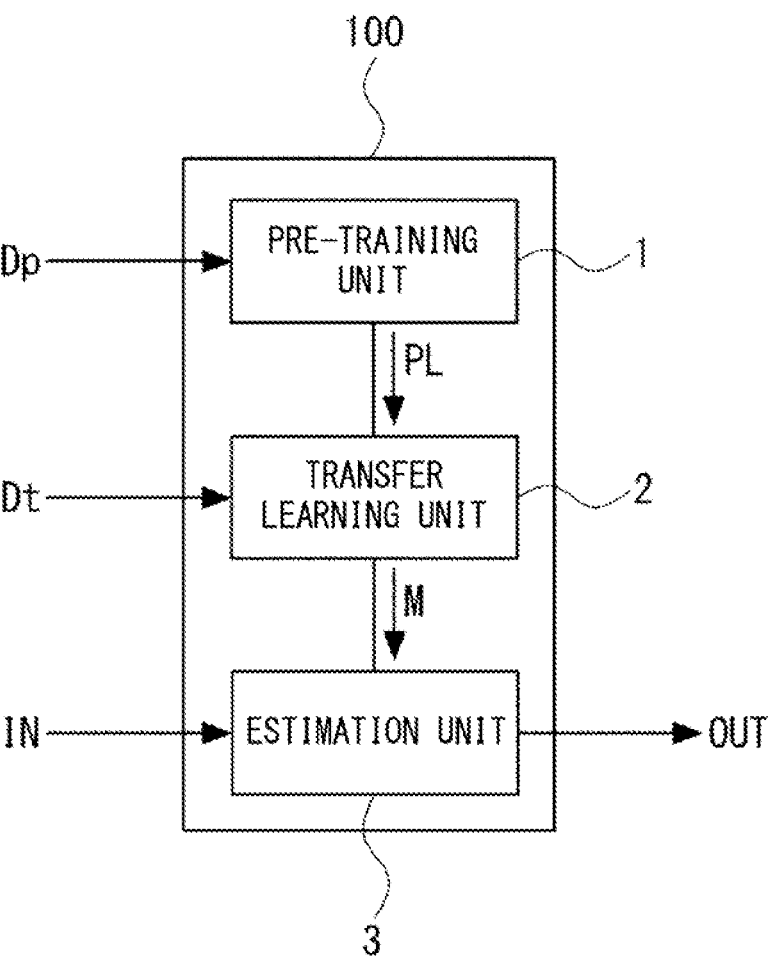
FIG. 1 is a diagram schematically illustrating a configuration of a body fluid volume estimation device according to a first example embodiment.

FIG. 1 schematically illustrates a configuration of the body fluid volume estimation device 100 according to the first example embodiment. The body fluid volume estimation device 100 includes a pre-training unit 1, a transfer learning unit 2, and an estimation unit 3.

The pre-training unit 1 receives pre-training data Dp described below, and performs pre-training that performs machine learning on a face image by using a body fluid volume label indicating a body fluid volume of a patient as a supervised label.

The transfer learning unit 2 reads, after completion of the pre-training, transfer learning data Dt described below that are formed of information about one specific patient being an estimation target of a body fluid volume, and performs transfer learning by using the face image. In this way, the transfer learning unit 2 can construct, based on the face image of the one specific patient being input separately, a trained model M that is used for estimating a body fluid volume.

The pre-training data Dp and the transfer learning data Dt may be provided from the outside of the body fluid volume estimation device 100 to the body fluid volume estimation device 100 via various communication means such as a network.

Figure 2:
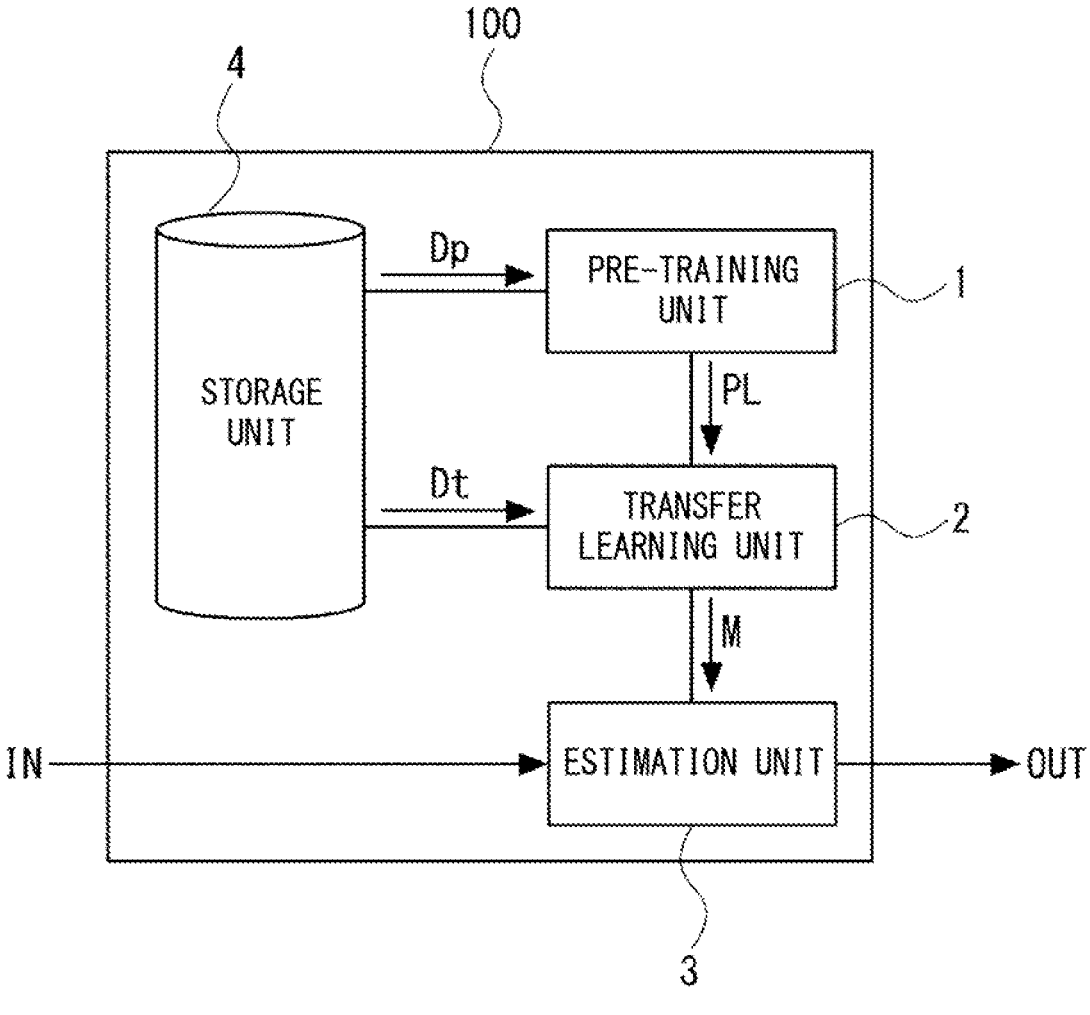
FIG. 2 is a diagram illustrating a modification example of the body fluid volume estimation device according to the first example embodiment.

Further, the pre-training data Dp and the transfer learning data Dt may be stored in advance in a storage unit provided in the body fluid volume estimation device 100. FIG. 2 schematically illustrates a modification example of the body fluid volume estimation device 100 according to the first example embodiment. As illustrated in FIG. 2, the body fluid volume estimation device 100 may further include a storage unit 4. The pre-training data Dp and the transfer learning data Dt are stored in advance in the storage unit 4. The pre-training unit 1 can appropriately read the pre-training data Dp from the storage unit 4. The transfer learning unit 2 can appropriately read the transfer learning data Dt from the storage unit 4. The information stored in the storage unit 4 may be provided from the outside of the storage unit 4 to the storage unit 4 via various communication means such as a network.

The estimation unit 3 estimates, by inputting a face image IN of one specific patient being captured at any point in time to the constructed trained model M, a body fluid volume of the patient at a point in time at which the face image IN is captured.

The face image IN may be provided from the outside of the body fluid volume estimation device 100 to the body fluid volume estimation device 100 via various communication means such as a network. In this case, the body fluid volume estimation device 100 is installed in a medical institution, for example, and thus a body fluid volume of a target patient can be estimated in the medical institution by transmitting a face image captured by the patient to the medical institution.

Figure 3:
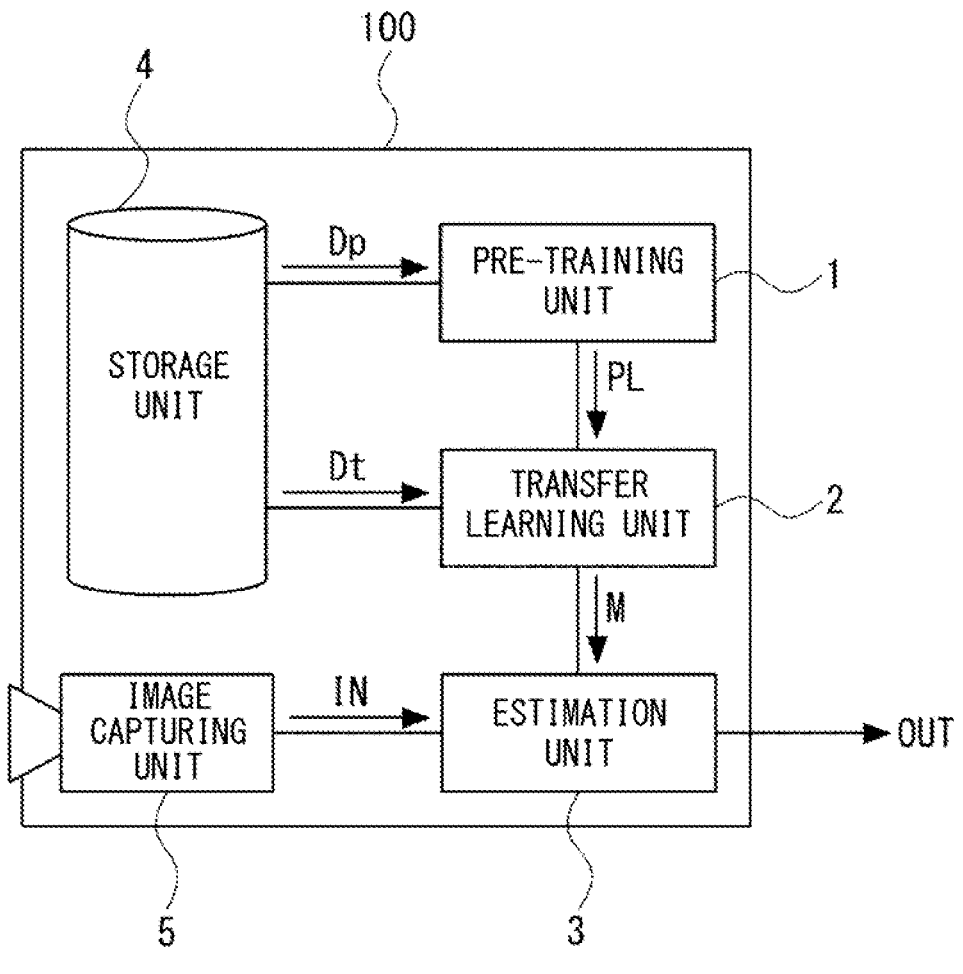
FIG. 3 is a diagram illustrating a modification example of the body fluid volume estimation device according to the first example embodiment.

Further, the face image IN may be an image captured by an image capturing unit provided in the body fluid volume estimation device 100. FIG. 3 schematically illustrates a modification example of the body fluid volume estimation device 100 according to the first example embodiment. As illustrated in FIG. 3, the body fluid volume estimation device 100 may further include an image capturing unit 5. The image capturing unit 5 may be various image capturing devices that can acquire an image, and can appropriately capture a face image of one specific patient at any point in time. The captured face image IN is appropriately input to the estimation unit 3. Note that the captured face image IN may be input to the estimation unit 3 via another non-illustrated processing unit, or may be read by the estimation unit 3 after the face image IN is stored in the storage unit 4.

As illustrated in FIG. 3, the pre-training unit 1, the transfer learning unit 2, the estimation unit 3, the storage unit 4, and the image capturing unit 5 are provided in one body fluid volume estimation device 100, and thus the body fluid volume estimation device 100 can be mounted on various portable terminals such as a smartphone on which an image capturing device such as a camera is mounted, for example.

Hereinafter, in the present example embodiment, it is assumed that a body fluid volume of a patient is estimated by estimating whether a swelling occurs in a face of the patient, and by predicting weight of the patient at a capturing point in time of a face image. Further, in the present example embodiment, it is assumed that a dialysis patient is a target, and whether a face image is captured before dialysis in which a swelling occurs or after dialysis in which a swelling does not occur is estimated in order to clearly distinguish whether a swelling occurs in a face of the patient.

In this way, when a state in which a swelling does not occur, i.e., a state after dialysis is set as a normal state, whether a body fluid volume of a patient is significantly changed from the normal state can be detected by estimating whether a swelling occurs in an input face image. When a swelling is estimated to occur in an input face image of a patient being an estimation target, for example, the estimation unit 3 may output, as a detection result, an increase in body fluid volume as compared to the normal state. Further, the estimation unit 3 may estimate a change amount of a body fluid volume from estimated weight, and output an estimation result. Such estimation result and detection result may be displayed on, for example, a non-illustrated display device (for example, an output unit 1007 in FIG. 13), and may be appropriately displayed on a screen when the body fluid volume estimation device 100 is mounted on a smartphone.

Next, the pre-training data Dp will be described. The pre-training data Dp are configured to include a plurality of records including a face image of a patient, label information (may also be simply referred to as a dialysis label) representing that the patient when the face image is captured before or after dialysis, and label information (may also be simply referred to as a weight label) indicating weight when the face image is captured. In other words, one record includes a face image of one patient, a dialysis label, and a weight label.

For example, in a case of a dialysis patient, a value acquired by subtracting a body fluid volume removed from a body of the patient by the dialysis from a value of a weight label associated with a face image of the patient before the dialysis may be used as a weight label associated with a face image after the dialysis. In this case, as compared to a case where weight of the patient after the dialysis is measured, a change in body fluid volume can be more accurately reflected in a weight label associated with a face image of the patient after the dialysis.

Further, for example, a value acquired by adding a body fluid volume removed from a body of a patient by dialysis to a weight label associated with a face image of the patient after the dialysis may be used as a weight label associated with a face image before the dialysis. In this case, as compared to a case where weight of the patient after the dialysis is measured, a change in body fluid volume can be more accurately reflected in a weight label associated with a face image of the patient before the dialysis. Further, a standard weight of a patient after dialysis, i.e., a patient in which a swelling does not occur, may be predetermined in advance for each patient, and a value acquired by adding a body fluid volume removed from a body of the patient by the dialysis to the standard weight may be used as a weight label associated with a face image before the dialysis of the patient.

Next, the transfer learning data Dt will be described. The transfer learning data Dt are configured to include a plurality of records including a face image of one specific patient being an estimation target of classification before and after dialysis and a prediction target of weight in the body fluid volume estimation device 100, dialysis label information, and a weight label. A configuration of each of the records is similar to that of the pre-training data Dp.

In the present example embodiment, it is assumed that the number of the records included in the pre-training data Dp is greater than the number of the records included in the transfer learning data Dt.

A dialysis label is a discrete label indicating a patient when a face image is captured is before or after dialysis, and may be, for example, "1" when an associated face image is a face image captured before dialysis with a swelling, and "0" when an associated face image is a face image captured after dialysis without a swelling.

In contrast, a weight label of a dialysis patient is provided as a numerical value, i.e., a continuous label indicating weight of the dialysis patient when an associated face image is captured.

A face image included in each record may be acquired by, for example, the pre-training unit 1 reading an original image including a face of a dialysis patient being captured in advance, and performing appropriate image processing. For example, the pre-training unit 1 performs face detection on an original image, and then estimates a central portion of a face. Then, the pre-training unit 1 may perform data augmentation such as resizing of an image, horizontal flipping, color conversion of an image, and gray scaling on the extracted face image as necessary, and may thus set the extracted face image as a face image of each record. Such data augmentation may be performed by the pre-training unit 1, or may be performed by an image processing unit provided separately from the pre-training unit 1.

Figure 4:
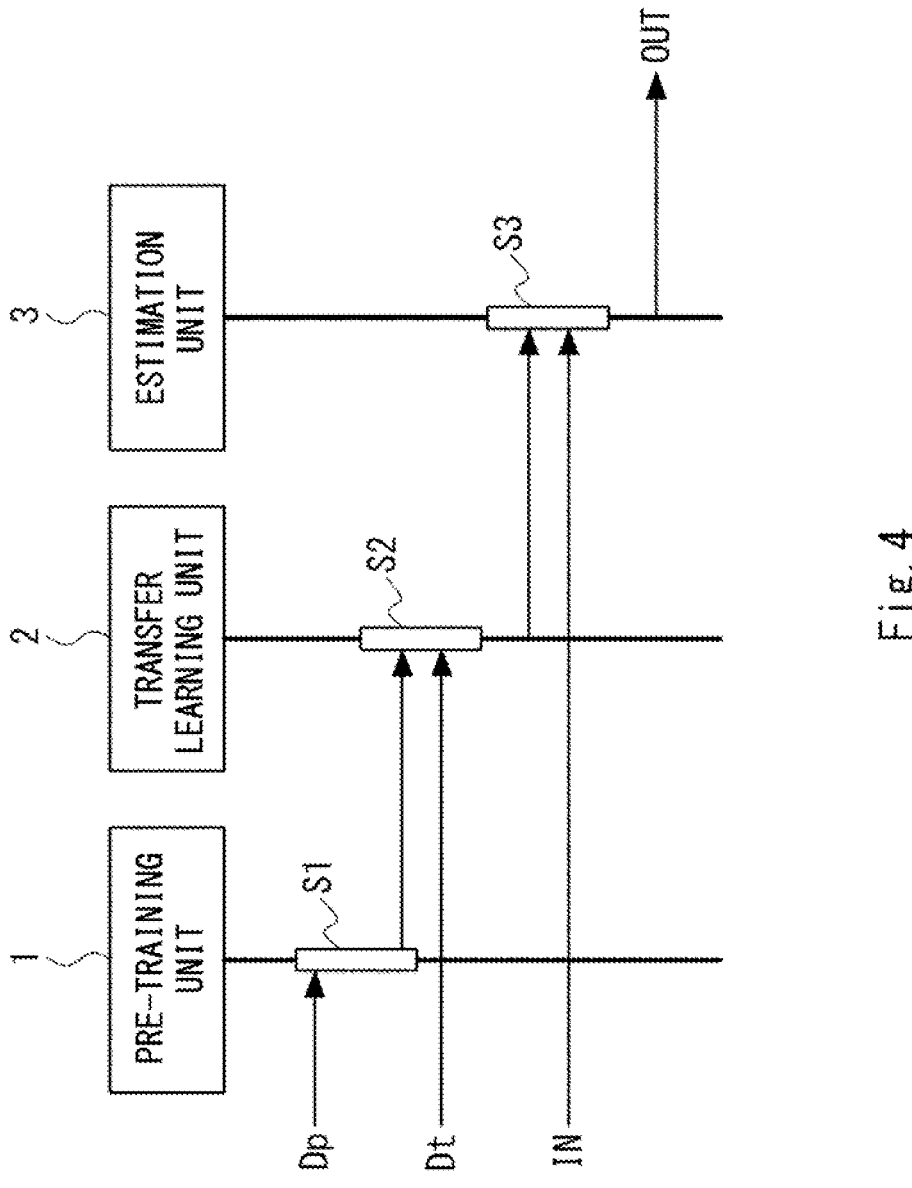
FIG. 4 is a diagram illustrating a sequence of processing of the body fluid volume estimation device according to the first example embodiment.

Next, a flow and a processing content of contrastive learning processing of the body fluid volume estimation device 100 will be described. As described above, the body fluid volume estimation device 100 performs the pre-training by WeightSupMoCo by using the pre-training data Dp about an unspecified large number of patients as input data, and the transfer learning by using the transfer learning data Dt about one specific patient being an estimation target as input data. FIG. 4 illustrates a sequence of processing of the body fluid volume estimation device 100 according to the first example embodiment.

Step S1: Pre-Training

In the pre-training, the body fluid volume estimation device 100 performs the pre-training by WeightSupMoCo by using the pre-training data Dp about an unspecified large number of patients as input data.

In the pre-training, contrastive learning based on Momentum Contrast (MoCo, Kaiming He et al., "Momentum Contrast for Unsupervised Visual Representation Learning", in Proc. IEEE/CVF conf. computer vision and pattern recognition (CVPR), 2020, pp. 9729-9738.) is performed. However, self-supervised learning without using a supervised label is performed in the contrastive learning by original MoCo, whereas, in the present example embodiment, as described above, the contrastive learning by Weight-SupMoCo is performed by using a dialysis label and a weight label as supervised labels.

Figure 5:
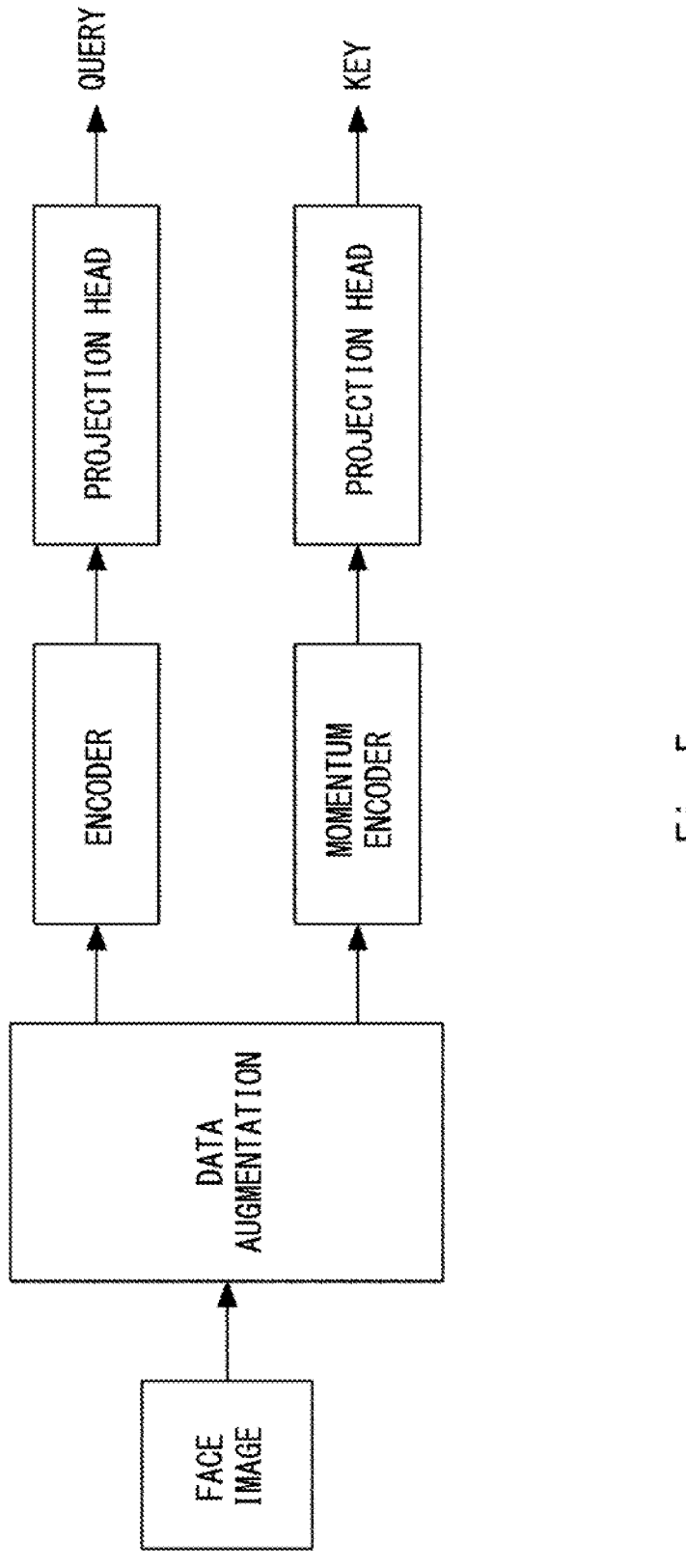
FIG. 5 is a diagram illustrating an overview of pre-training by weight-aware supervised momentum contrast (WeightSupMoCo) according to the first example embodiment.

FIG. 5 illustrates an overview of the pre-training by WeightSupMoCo according to the first example embodiment. In WeightSupMoCo, an encoder (feature extractor) and a momentum encoder are used, and a fully connected layer referred to as a projection head is provided in a subsequent stage of each of the encoders. A feature value being output from the projection head in the subsequent stage of the encoder is referred to as a query, and a feature value being output from the projection head in the subsequent stage of the momentum encoder is referred to as a key. The key is accumulated as a queue in a dictionary, and the contrastive learning is performed by using the query and the queue.

Meanwhile, the contrastive learning by Simple Framework for Contrastive Learning of Visual Representations (SimCLR, T. Chen, S. Kornblith, M. Norouzi, and G. Hinton, "A simple framework for contrastive learning of visual representations," Proc. Int. conf. machine learning (ICML), 2020, pp. 1597-1607.) using a normal encoder instead of the momentum encoder, and the like has also been known. Such a technique has a size of a dictionary equivalent to a mini-batch size, and has thus been known to have a disadvantage of a small number of samples with which the contrastive learning is performed.

Further, as a technique for the contrastive learning using a discrete supervised label such as a dialysis label, for example, a technique using Supervised Contrastive (Sup-Con) Loss (P. Khosla et al., "Supervised Contrastive Learning", in Proc. Advances in Neural Information Processing Systems (NeurIPS), vol. 33, pp. 18661-18673, 2020.) as a loss function has been known. As a technique for the contrastive learning using a continuous supervised label such as a weight label, for example, a technique using y-Aware InfoNCE Loss (B. Dufumier et al., "Contrastive Learning with Continuous Proxy Meta-Data for 3D MRI Classification", in Int. Conf. Medical Image Computing and Computer-Assisted Intervention (MICCAI), 2021, pp. 58-68.) as a loss function has been known. However, the techniques using SupCon Loss and y-Aware InfoNCE Loss are SimCLR-type techniques, and have a disadvantage of a small number of samples with which the contrastive learning is performed, as described above.

In contrast, in the present example embodiment, an MoCo-type WeightSupMoCo Loss is used as a loss function when the contrastive learning is performed by using a discrete dialysis label and a continuous weight label as supervised labels. Thus, unlike the SimCLR-type technique, the contrastive learning can be performed by increasing a size of a dictionary, and acquisition of better feature representation can be achieved.

Next, WeightSupMoCo according to the present example embodiment will be described in more detail. In Weight-SupMoCo, when labels before and after dialysis are the same, contrastive learning is performed in such a way that feature representation of face images is brought closer according to a degree of similarity to a weight label. Hereinafter, a specific description will be given. The reason is that a degree of a swelling may be conceivably more similar when states of presence and absence of a swelling are the same between face images before dialysis or between face images after dialysis, and a degree of a swelling may be more similar when weights are similar.

Hereinafter, a specific description will be given. When a weight label is y, a dialysis label is a, and a feature value being output from the projection head is z, a Weight-SupMoCo Loss is represented by the following expression.

$$L_i = $$

[Mathematical 1]

$$-\sum_{k \in A(i)} \frac{w_\sigma(y_i, y_k) \cdot \delta_{a_i=a_k}}{\sum_{j \in A(i)} w_\sigma(y_i, y_j) \cdot \delta_{a_i=a_j}} \cdot \frac{\exp(z_i \cdot z_k / \tau)}{\sum_{j \in A(i)} \exp(z_i \cdot z_j / \tau)}$$

Note that A(i) is a group of a mini-batch of queries and queues except for an i-th record. $w_\sigma(\bullet, \bullet)$ is a function representing a degree of similarity of a weight label, and a radial basis function (RBF) kernel described in "B. Dufumier et al., "Contrastive Learning with Continuous Proxy Meta-Data for 3D MRI Classification", in Int. Conf. Medical Image Computing and Computer-Assisted Intervention (MICCAI), 2021, pp. 58-68." is used herein. $\sigma$ is a hyper parameter of the RBF kernel, and $\sigma=3.0$. $\tau$ is a temperature parameter, and $\tau=0.1$ herein.

$$\delta_{a_i=a_j}$$

[Mathematical 2]

is a function that replies "1" when a label $a_i$ and a label $a_j$ have the same value ($a_i=a_j$), and replies "0" in the other cases. Further, a dictionary size of a queue is assumed to be 1024. Since the feature value z is a Euclidean distance 1, an inner product of feature values is equivalent to a cosine similarity degree.

Figure 6:
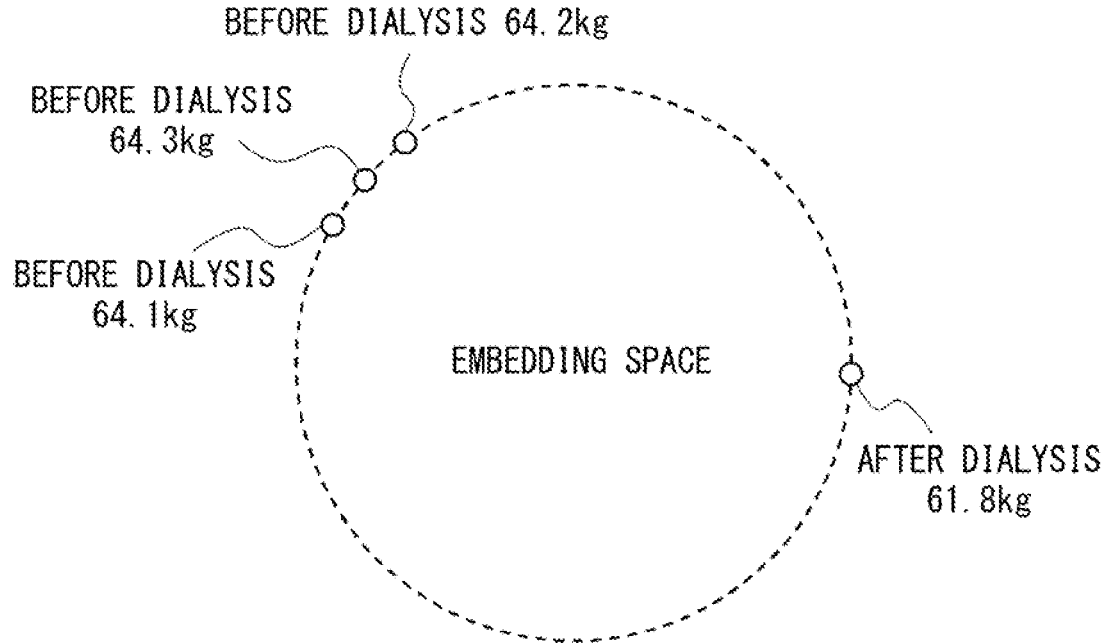
FIG. 6 is a diagram illustrating an overview of face images before and after dialysis in an embedding space after the pre-training.

FIG. 6 illustrates an overview of face images before and after dialysis in an embedding space after the pre-training. As illustrated in FIG. 6, as a result of the pre-training, face images having the same dialysis label "before dialysis" in the embedding space are distributed at a short distance in the embedding space. In contrast, face images having the same dialysis label "after dialysis" are distributed in relatively distant positions from the face images having the same dialysis label "before dialysis".

Further, in the embedding space, face images having the same dialysis label are distributed according to a degree of similarity of a weight label, i.e., are distributed at a shorter distance with more similar weight labels and are distributed at a farther distance with less similar weight labels.

Step S2: Transfer Learning

Figure 7:
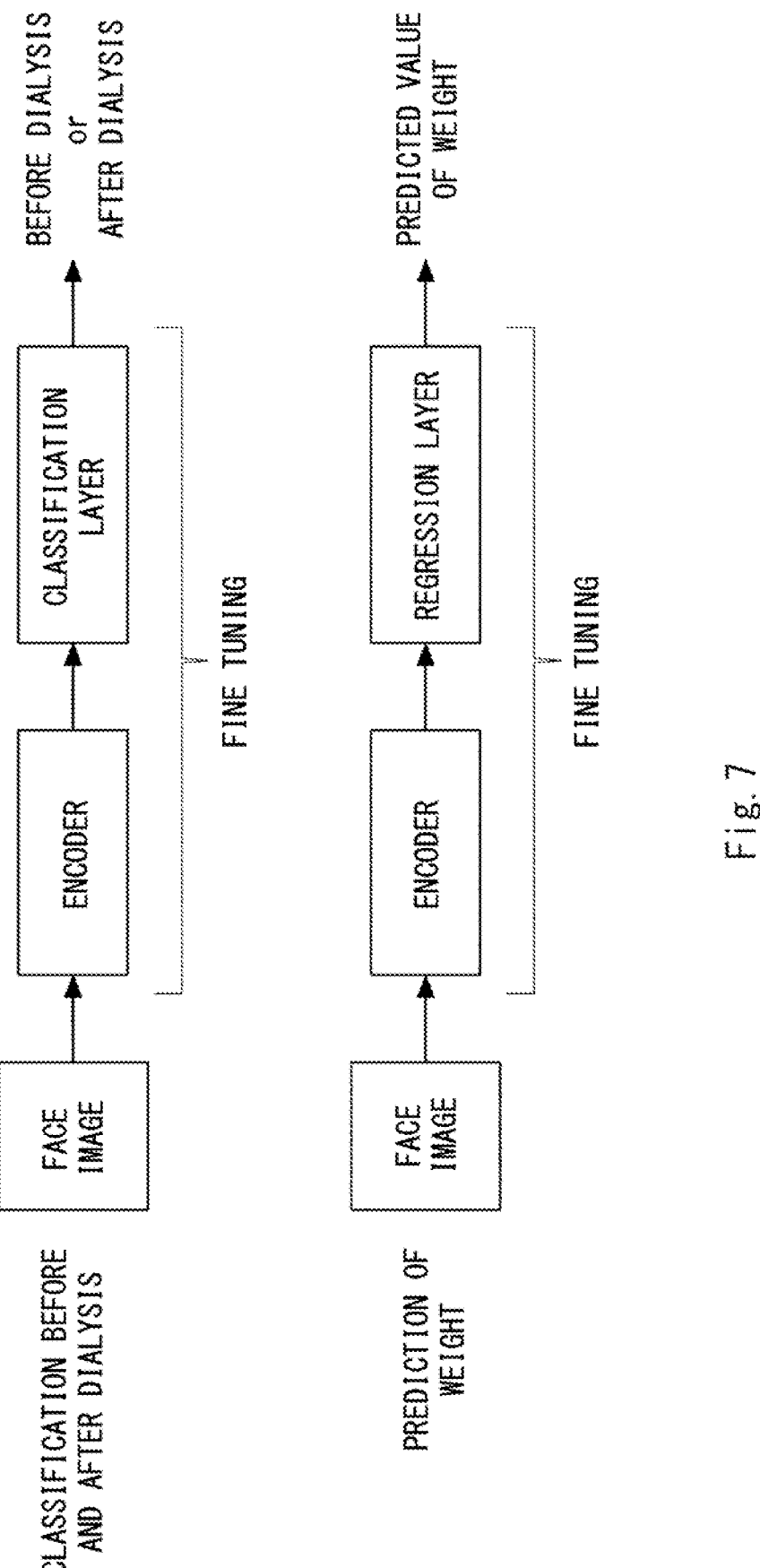
FIG. 7 is a diagram illustrating an overview of transfer learning according to the first example embodiment.

Subsequently, the transfer learning unit 2 performs the transfer learning by using a result PL of the pre-training by using, as input data, the transfer learning data Dt about one specific patient being an estimation target. In the present example embodiment, in the transfer learning, only the encoder is used without using the projection head used in the pre-training. FIG. 7 illustrates an overview of the transfer learning according to the first example embodiment. In this way, one linear layer formed of a classification layer and a regression layer is added to a subsequent stage of the encoder. In the classification layer, the number of dimensions of output in classification before and after dialysis using the transfer data Dt being data about one specific patient is 2. In the regression layer, the number of dimensions of output in weight prediction is 1.

Then, fine tuning that performs transfer learning on the encoder and all of the added linear layers is performed by using the data about the one specific patient. Herein, as a loss function in the fine tuning, a cross entropy loss is used for classification before and after dialysis, and a mean square error loss is used for weight prediction.

Step S3: Estimation

The trained model M is constructed by performing the procedures described above. By inputting the face image IN of the one specific patient being the estimation target to the trained model M, the estimation unit 3 can estimate whether the patient extracted from the face image is before or after dialysis (presence or absence of a swelling), and predict weight of the patient, and can output the estimation result OUT.

By the procedures described above, the trained model can be constructed by performing the pre-training using data about an unspecified large number of patients and the transfer learning using data about one specific patient. Then, by inputting a face image of the one specific patient to the trained model, whether the patient is before or after dialysis (presence or absence of a swelling), and weight can be predicted.

Next, a comparison experiment with a general technique was performed in order to verify significance of a technique in the present example embodiment. Hereinafter, an experiment condition and an experiment result will be described.

In the pre-training, randomly selected 80% of data acquired from multiple patients was used as the pre-training data Dp, and remaining 20% was used as validation data.

In the transfer learning and estimation, multiple groups of face images before and after dialysis of one specific patient were acquired on several different dialysis opportunities. One of the groups was used as the test data. Among the groups other than the test data, 80% of the randomly selected groups were used as the transfer learning data Dt and the remaining 20% was used as validation data. Note that an opportunity for a patient to receive dialysis is referred to as a dialysis opportunity, but dialysis is normally performed within one day (generally, approximately four hours), and thus the dialysis opportunity will be simply referred to as a dialysis day below. Further, in the present experiment, it is assumed that the one specific patient used for the transfer learning and the estimation is not included among the multiple patients used for the pre-training.

The face images used in this experiment were resized to 224×224 pixels, and data augmentation was performed including flipped horizontally, color conversion, and grayscaling. In the present experiment, training of 100 epochs in the pre-training and 20 epochs in the transfer learning was performed. However, a model in which a validation data error in the pre-training is the smallest epoch was used for the transfer learning in a subsequent stage. As an optimization algorithm, Adam (D. P. Kingma and J. Ba, "ADAM: A METHOD FOR STOCHASTIC OPTIMIZATION," arXiv preprint arXiv: 1412.6980, 2014.) was used, a learning rate of the pre-training was set as $10^{-4}$, and a learning rate of the transfer learning was set as $10^{-3}$. In the prediction of weight in the transfer learning, the learning and the prediction were performed with weight being normalized into a mean 0 and a variance 1.

In the present experiment, the following techniques were used as comparative examples for comparison with the technique according to the present example embodiment.

First Comparative Example

In order to verify effectiveness of the pre-training, a technique (without the pre-training) for performing training only with data about one specific patient without performing the pre-training was set as a first comparative example.

Second Comparative Example

In order to verify effectiveness when a supervised label was used, SimCLR in a self-supervised learning technique was set as a second comparative example.

Third Comparative Example

In order to verify effectiveness when a supervised label was used, MoCo in a self-supervised learning technique was set as a third comparative example.

Fourth Comparative Example

Similarly, as a pre-training technique using general normal supervised learning, a classification technique using a dialysis label based on a cross entropy loss was set as a fourth comparative example.

Fifth Comparative Example

In order to verify effectiveness of the pre-training based on the technique (WeightSupMoCo) according to the present example embodiment, a case where the pre-training technique based on SupCon using a dialysis label as discrete supervised information was used was set as a fifth comparative example.

Sixth Comparative Example

Similarly, in order to verify effectiveness of the pre-training based on the technique (WeightSupMoCo) according to the present example embodiment, a case where the pre-training technique based on y-Aware InfoNCE using a weight label as continuous supervised information was used was set as a sixth comparative example.

As an evaluation indicator in classification before and after dialysis, Accuracy, area under the receiver operating characteristic curve (ROC-AUC), and area under the precision-recall curve (PR-AUC) of an estimated label were used. Further, as an evaluation indicator in weight prediction, a mean absolute error (MAE), a root mean squared error (RMSE), and a correlation coefficient (CorrCoef) between a predicted value of weight and ground-truth data were used.

Experiment Result

FIG. 8 illustrates estimation performance of classification before and after dialysis and weight prediction in each technique. It could be confirmed from FIG. 8 that Weight-SupMoCo according to the present example embodiment can estimate classification before and after dialysis and predict weight with higher performance than that of any of the comparative techniques.

First, it could be understood from comparison between the technique ("without pre-training" in FIG. 8) without performing the pre-training and the other techniques that effectiveness for performing the pre-training was significant. Further, effectiveness for using a dialysis label and weight of a dialysis patient as supervised data about a body fluid volume could be confirmed from comparison between SimCLR and MoCo being the self-supervised learning techniques and WeightSupMoCo according to the present example embodiment. Furthermore, effectiveness for using a dialysis label and a weight label in a cooperative manner and effectiveness for increasing a size of a dictionary by a MoCo type could also be confirmed from comparison between WeightSupMoCo, and SupCon and y-Aware InfoNCE.

Figure 9:
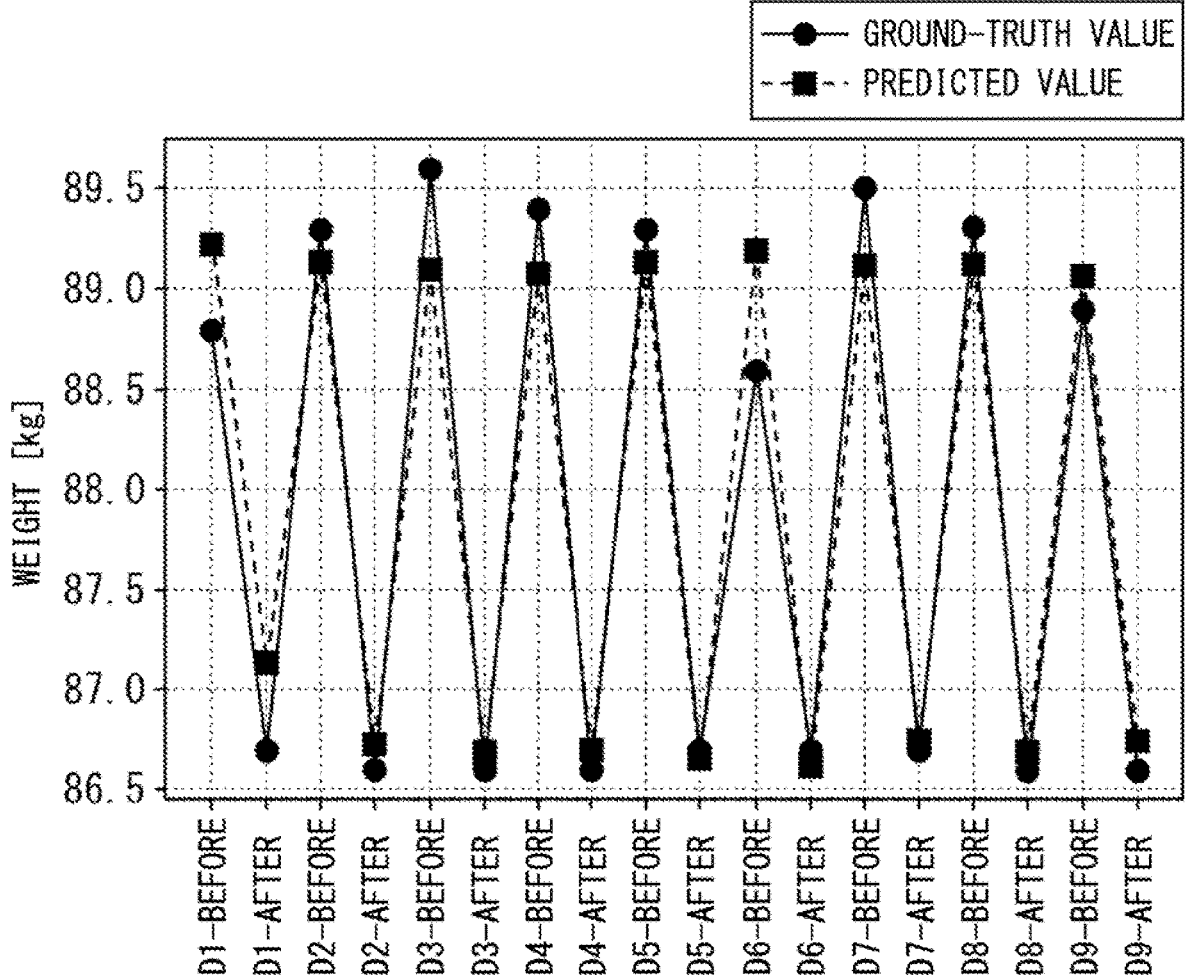
FIG. 9 is a diagram illustrating a transition of estimated weight and ground-truth weight of a patient having the highest estimation performance.
Figure 10:
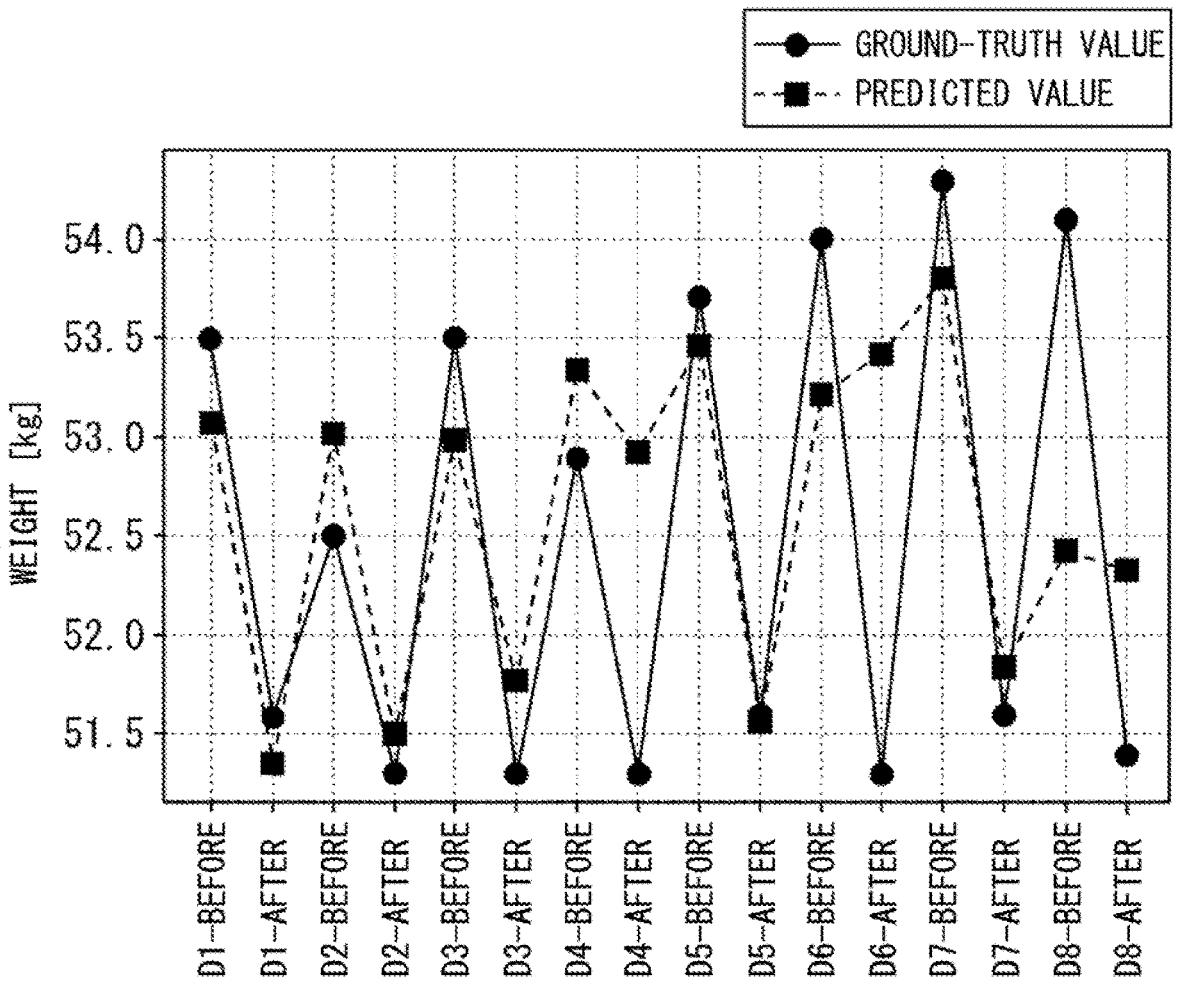
FIG. 10 is a diagram illustrating a transition of estimated weight and ground-truth weight of a patient having the lowest estimation performance.

Next, a transition of estimated weight and ground-truth weight for a dialysis opportunity will be considered. FIG. 9 illustrates a transition of estimated weight and ground-truth weight of a patient having the highest estimation performance. It could be confirmed from FIG. 9 that a transition of weight could be predicted with high performance. Further, FIG. 10 illustrates a transition of estimated weight and ground-truth weight of a patient having the lowest estimation performance. It could be confirmed that some patients had a dialysis opportunity with low performance of estimated weight but an increase and a decrease in weight before and after dialysis could be suitably predicted. Thus, it could be understood that weight representing a degree of a swelling could be predicted from a face image of a dialysis patient.

Figure 11:
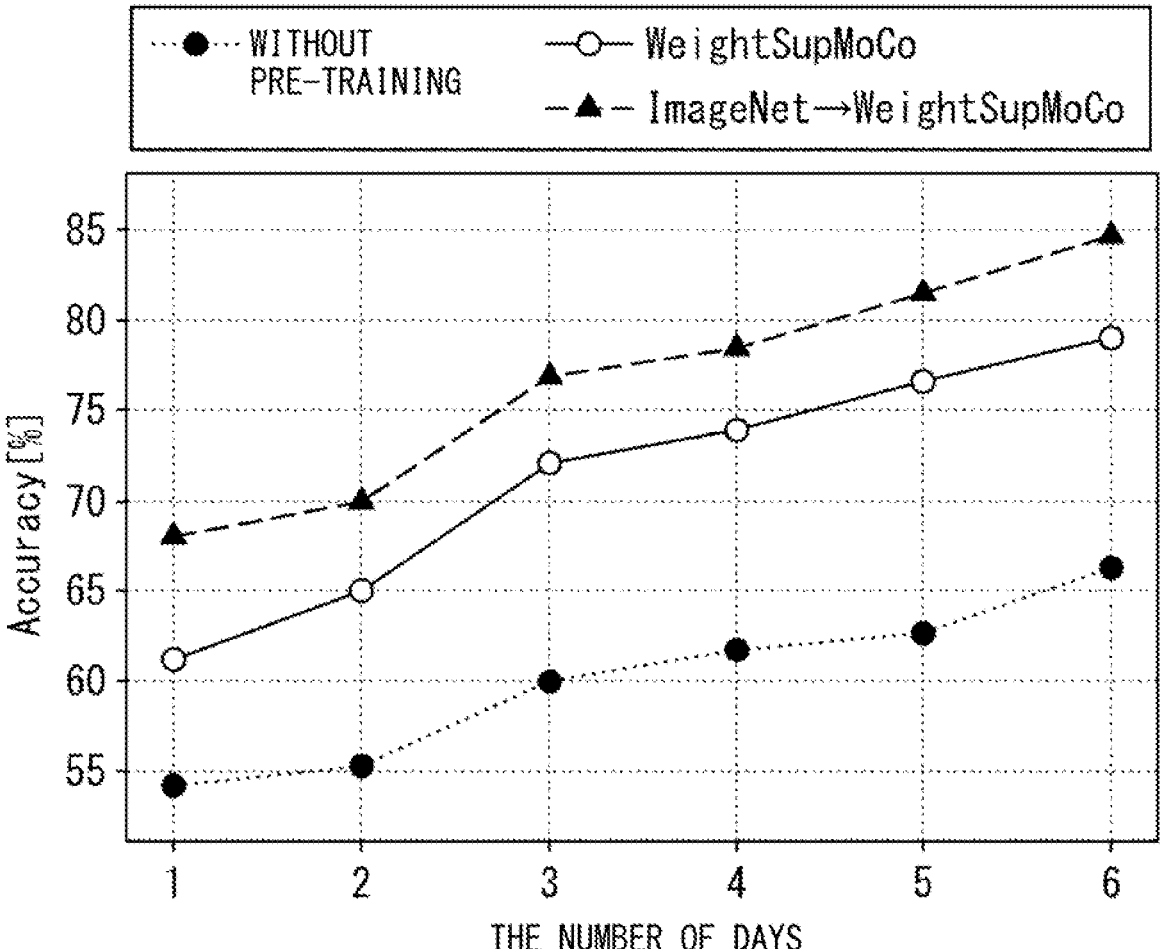
FIG. 11 is a diagram illustrating a change in accuracy of classification before and after dialysis with respect to the number of days of transfer learning data.
Figure 12:
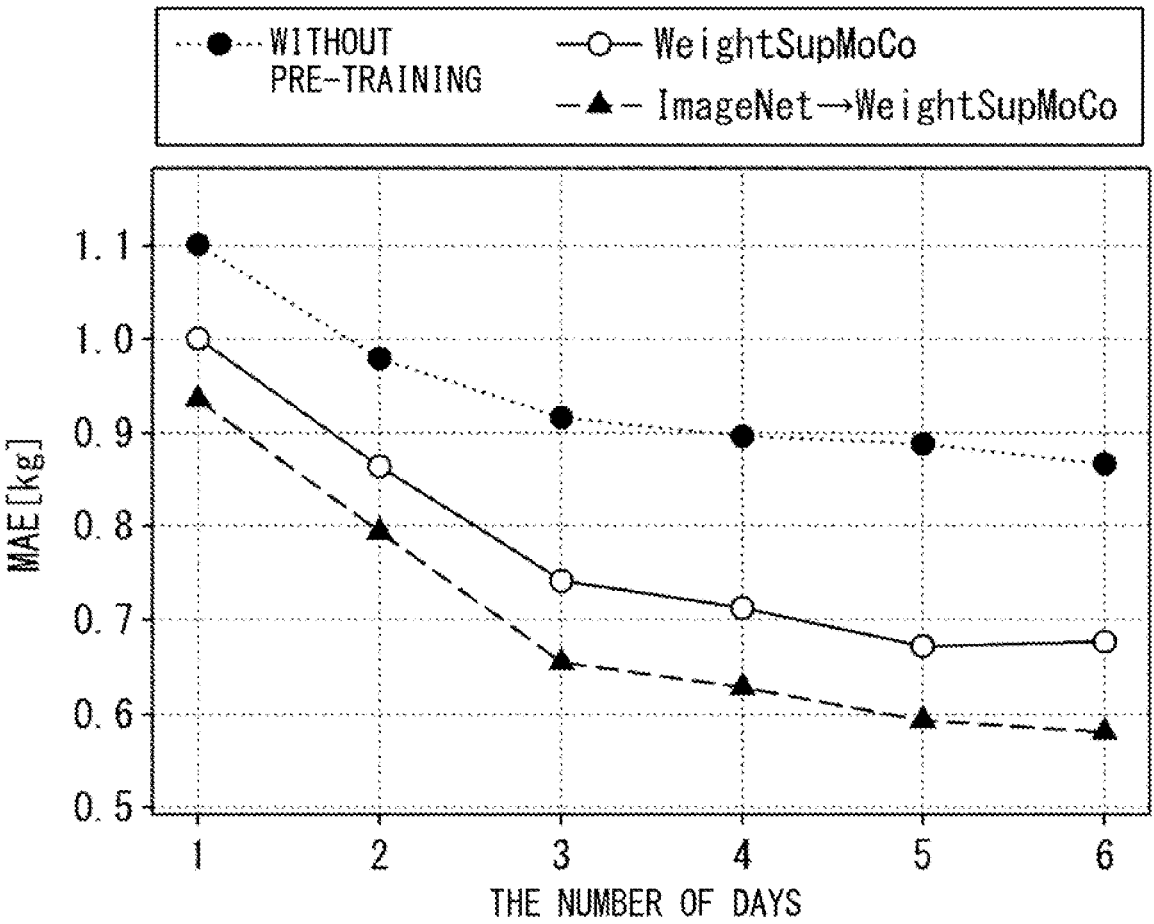
FIG. 12 is a diagram illustrating a change in mean absolute error (MAE) of weight estimation with respect to the number of days of the transfer learning data.

Next, estimation performance of classification before and after dialysis and weight prediction with respect to the number of days of training data used in the transfer learning will be considered. FIG. 11 illustrates a change in Accuracy being the estimation performance of the classification before and after dialysis with respect to the number of days of the transfer learning data. FIG. 12 illustrates a MAE change being the estimation performance of the weight estimation with respect to the number of days of the transfer learning data. In FIGS. 11 and 12, a technique without performing the pre-training (without the pre-training), a technique for performing the pre-training based on WeightSupMoCo, and a technique (Image Net→WeightSupMoCo) for performing the pre-training on the model pre-trained with ImageNet (J. Deng, W. Dong, R. Socher, L. Li, et al., "ImageNet: A Large-Scale Hierarchical Image Database", Proc. IEEE/CVF conf. computer vision and pattern recognition (CVPR), 2009), based on WeightSupMoCo, were compared.

In all of the techniques, the estimation performance was improved as the number of days of the transfer training learning data was increased. Further, when the technique without the pre-training was compared with the other techniques, it could be confirmed that effectiveness for performing the pre-training was significant.

Further, it could be confirmed that ImageNet→WeightSupMoCo was the most accurate and it was effective to perform the pre-training on the model pre-trained with ImageNet, based on WeightSupMoCo.

Since it is desirable that the number of days of training data about one specific patient constituting the transfer learning data is as small as possible, it can be understood that estimation with relatively high performance in which Accuracy of the classification before and after dialysis is 76.8% and MAE in the weight prediction is 0.65 kg can be achieved by using the transfer learning data in a relatively short period of three days by performing the pre-training (ImageNet-→WeightSupMoCo).

As described above, the body fluid volume estimation device 100 can not only determine presence or absence of a swelling from a face image of a patient, but can also predict weight of the dialysis patient and estimate a body fluid volume in a body, i.e., a degree of a swelling of the dialysis patient. Further, since training is performed by using a dialysis label and a weight label, and estimation is performed by using the training result, a variation in swelling level and the like by a viewpoint of a doctor can be reduced unlike a previous diagnosis, and a more objective diagnostic result can be acquired.

Further, the number of pieces of data such as a face image that can be acquired, presence or absence of a swelling, and weight is limited from only one specific patient, but, according to the present configuration, the pre-training is performed by data acquired from an unspecified large number of patients, and thus a sufficient amount of training data can be used in order to achieve high estimation performance.

As illustrated in FIG. 3, by incorporating an image capturing means of a face image into the body fluid volume estimation device 100, a patient captures his/her own face image at any place (for example, at home) and any point in time, and performs estimation by the body fluid volume estimation device 100, and can thus recognize presence or absence of occurrence of his/her own swelling and a degree of the swelling, i.e., a body fluid volume. In this way, a dialysis patient can appropriately and easily confirm his/her own body fluid volume at appropriate time. Further, the present configuration is advantageous over a general inspection technique in a point that involvement of health care professionals and special mechanical equipment are unnecessary.

According to the present configuration, whether a state of a patient is closer to a state in which a swelling occurs or a state in which a swelling does not occur can be recognized by using a prediction score representing presence or absence of a swelling being acquired from an estimation result of presence or absence of a swelling. Further, by using estimated weight, a patient himself/herself can recognize a degree of a swelling, and estimate the amount of water in a body. Furthermore, a patient himself/herself can perform an adjustment of the amount of food and a water intake, selection of a menu of a meal, and an adjustment of the amount of medicine (such as a diuretic) and the like, based on a score representing presence or absence of an estimated swelling, weight, and the like.

Even when a patient cannot go to a medical institution such as a hospital (for example, in a remote area), by transmitting information indicating a body fluid volume estimated by the body fluid volume estimation device 100 to a doctor and the like in the medical institution, the doctor and the like can recognize the body fluid volume of the patient with high performance, and can also give an accurate diagnosis and life guidance.

OTHER EXAMPLE EMBODIMENT

Note that the present disclosure is not limited to the example embodiment described above, and may be appropriately modified without departing from the scope of the present disclosure. For example, in the example embodiment described above, a dialysis label and a weight label are used as supervised labels, but another discrete label and another continuous label may be appropriately used in combination.

Further, description is given on an assumption that one kind of a discrete label and one kind of a continuous label are used, but any number of each of a kind of a discrete label and a kind of a continuous label can be used.

In the example embodiment described above, a dialysis patient is focused, but it is needless to say that the body fluid volume estimation device 100 may be applied to estimation of an occurrence situation of a swelling of a patient having another disease in which a swelling occurs.

In the example embodiment described above, description is given on an assumption that presence or absence of occurrence of a swelling is estimated, which is merely an exemplification. A situation of a change in face image other than a swelling due to a disease and the like, for example, a change in size and shape of a face other than a swelling due to heatstroke and the like, a change in complexion, and the like can also be estimated.

Although the configuration of the body fluid volume estimation device 100 has been described above as a configuration of hardware in the example embodiment described above, the present disclosure is not limited to the example embodiment. The processing in the body fluid volume estimation device 100 can also be achieved by causing a central processing unit (CPU) to execute a computer program. Further, the program described above is stored by using a non-transitory computer-readable medium of various types, and can be supplied to a computer. The non-transitory computer-readable medium includes a tangible storage medium of various types. Examples of the non-transitory computer-readable medium include a magnetic recording medium (for example, a flexible disk, a magnetic tape, and a hard disk drive), a magneto-optical recording medium (for example, a magneto-optical disk), a CD-read only memory (CD-ROM), a CD-R, a CD-R/W, and a semiconductor memory (for example, a mask ROM, a programmable ROM (PROM), an erasable PROM (EPROM), a flash ROM, and a random access memory (RAM)). Further, a program may be supplied to a computer by a transitory computer-readable medium of various types. Examples of the transitory computer-readable medium include an electrical signal, an optical signal, and an electromagnetic wave. The transitory computer-readable medium may supply the program to the computer via a wired communication path such as an electric wire and an optical fiber or a wireless communication path.

One example of the computer is described below. As the computer, various computers such as a dedicated computer and a personal computer (PC) can be achieved. However, the computer does not need to be physically single, and may be plural when distributed processing is performed.

Figure 13:
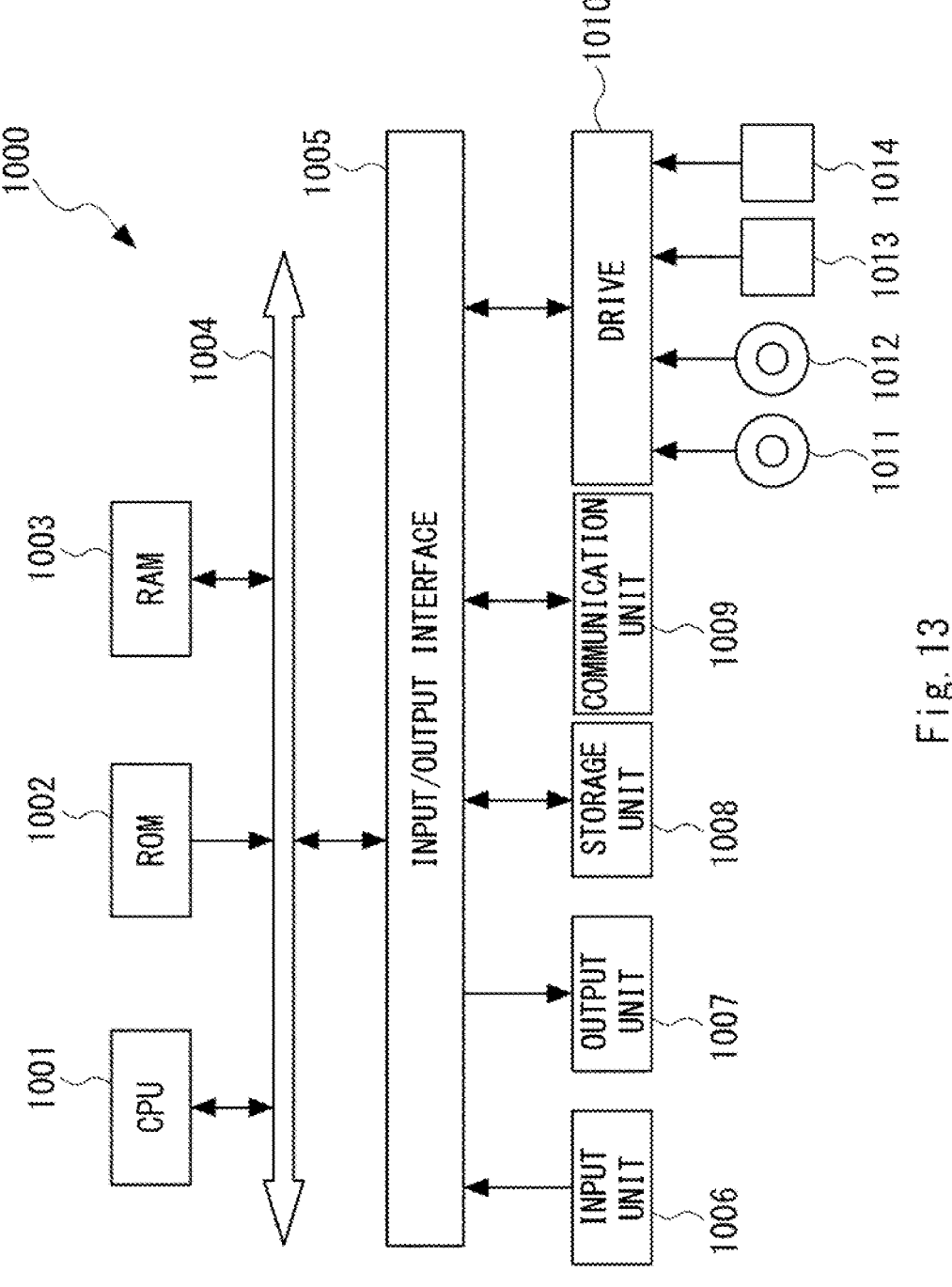
FIG. 13 is a diagram illustrating a configuration example of a computer.

FIG. 13 illustrates a configuration example of a computer. A computer 1000 in FIG. 13 includes a central processing unit (CPU) 1001, a read only memory (ROM) 1002, and a random access memory (RAM) 1003, and these are connected to one another via a bus 1004. Note that description of OS software and the like for operating the computer will be omitted, but the computer includes the OS software and the like as a matter of course.

An input/output interface 1005 is also connected to the bus 1004. For example, an input unit 1006 formed of a keyboard, a mouse, a sensor, and the like, an output unit 1007 formed of a display formed of a CRT, an LCD, and the like, a headphone, a speaker, and the like, a storage unit 1008 formed of a hard disk and the like, a communication unit 1009 formed of a modem, a terminal adapter, and the like, and the like are connected to the input/output interface 1005.

The CPU 1001 executes various programs stored in the ROM 1002, various types of processing according to various programs loaded from the storage unit 1008 into the RAM 1003, and, for example, processing of each unit of the body fluid volume estimation device 100 in the example embodiment described above. Note that a graphics processing unit (GPU) may be provided, and similarly to the CPU 1001, the GPU may execute various programs stored in the ROM 1002, various types of processing according to various programs loaded from the storage unit 1008 into the RAM 1003, and, for example, processing of each unit of the body fluid volume estimation device 100 in the present example embodiment described above. Note that the GPU is suitable for use for performing pieces of typical processing in parallel, and, by applying the GPU to processing and the like in a neural network described below, a processing speed can be improved as compared to the CPU 1001. Data and the like needed for the CPU 1001 and the GPU to perform various types of processing are also appropriately stored in the RAM 1003.

For example, the communication unit 1009 performs communication processing via the Internet (not illustrated), transmits data provided from the CPU 1001, and outputs data received from a communication partner to the CPU 1001, the RAM 1003, and the storage unit 1008. The storage unit 1008 communicates with the CPU 1001, and stores and deletes information. The communication unit 1009 performs communication processing of an analog signal or a digital signal with another device.

A drive 1010 is connected to the input/output interface 1005 as necessary, and, for example, a magnetic disk 1011, an optical disk 1012, a flexible disk 1013, a semiconductor memory 1014, or the like is appropriately mounted, and a computer program read from that is installed in the storage unit 1008 as necessary.

The present disclosure has been described above, and the present disclosure can also be described as follows.

(Supplementary Note 1)

A body fluid volume estimation device including:

a pre-training unit configured to perform pre-training on face images of multiple patients by using, as supervised information, information indicating a body fluid volume of each of the plurality of patients when the face images of the plurality of patients are captured;

a transfer learning unit configured to further perform transfer learning on multiple face images of one specific patient after the pre-training, and construct a trained model; and an estimation unit configured to estimate, by inputting a face image of the one specific patient to the trained model, a body fluid volume of the one specific patient at a point in time at which the face image of the one specific patient is captured.

(Supplementary Note 2)

The body fluid volume estimation device according to Supplementary Note 1, in which the information indicating the body fluid volume of each the plurality of patients when the face images of the plurality of patients are captured includes information indicating presence or absence of a swelling in the face image of each of the plurality of patients, and information indicating weight of each of the plurality of patients, and the estimation unit estimates presence or absence of a swelling and predicts weight of the one specific patient at a point in time at which the face image of the one specific patient is captured by inputting the face image of the one specific patient to the trained model.

(Supplementary Note 3)

The body fluid volume estimation device according to Supplementary Note 2, in which the estimation unit detects, based on an estimation result of the presence or absence of the swelling of the one specific patient, whether the body fluid volume of the one specific patient is changed from a preset standard body fluid volume of the one specific patient, and acquires, from an prediction result of the weight, a difference in the body fluid volume of the one specific patient from the standard body fluid volume.

(Supplementary Note 4)

The body fluid volume estimation device according to Supplementary Note 2 or 3, in which the information indicating the presence or absence of the swelling in the face image of each of the plurality of patients is label information representing the presence or absence of the swelling, and the pre-training unit performs pre-training in such a way that feature values of face images having the same label information representing the presence or absence of the swelling are brought closer as the information indicating the weight is more similar.

(Supplementary Note 5)

The body fluid volume estimation device according to any one of Supplementary Notes 2 to 4, in which the pre-training unit performs pre-training by weight-aware supervised momentum contrast (WeightSupMoCo).

(Supplementary Note 6)

The body fluid volume estimation device according to any one of Supplementary Notes 2 to 5, in which the plurality of patients and the one specific patient are a patient who receives dialysis, and weight of each of the plurality of patients and the one specific patient after dialysis associated with a case without a swelling has a value acquired by subtracting a body fluid volume removed by dialysis from weight of each of the plurality of patients and the one specific patient before dialysis associated with a case with a swelling.

(Supplementary Note 7)

The body fluid volume estimation device according to any one of Supplementary Notes 2 to 5, in which the plurality of patients and the one specific patient are a patient who receives dialysis, and weight of each of the plurality of patients and the one specific patient before dialysis associated with a case with a swelling has a value acquired by adding a body fluid volume removed by dialysis to weight of each of the plurality of patients and the one specific patient after dialysis associated with a case without a swelling.

(Supplementary Note 8)

The body fluid volume estimation device according to any one of Supplementary Notes 2 to 5, in which the plurality of patients and the one specific patient are a patient who receives dialysis, and weight of each of the plurality of patients and the one specific patient before dialysis associated with a case with a swelling has a value acquired by adding a body fluid volume removed by dialysis to preset standard weight of each of the plurality of patients and the one specific patient.

(Supplementary Note 9)

The body fluid volume estimation device according to any one of Supplementary Notes 1 to 8, further including a storage unit configured to store the face images of the plurality of patients to be used for pre-training, the information indicating the body fluid volume of the plurality of patients when the face images of the plurality of patients are captured, and the plurality of face images of the one specific patient to be used for the transfer learning, in which the pre-training unit reads, from the storage unit, the face images of the plurality of patients and information indicating the body fluid volume when the face images of the plurality of patients are captured, and performs pre-training, and the transfer learning unit reads, from the storage unit, the plurality of face images of the one specific patient, and performs transfer learning.

(Supplementary Note 10)

The body fluid volume estimation device according to any one of Supplementary Notes 1 to 9, further including an image capturing unit, in which a face image of the one specific patient being captured by the image capturing unit is input to the estimation unit.

(Supplementary Note 11)

A body fluid volume estimation method including:

performing pre-training on face images of multiple patients by using, as supervised information, information indicating a body fluid volume of each of the plurality of patients when the face images of the plurality of patients are captured;

further performing transfer learning on multiple face images of one specific patient after the pre-training, and constructing a trained model; and estimating, by inputting a face image of the one specific patient to the trained model, a body fluid volume of the one specific patient at a point in time at which the face image of the one specific patient is captured.

(Supplementary Note 12)

A program causing a computer to execute:

processing of performing pre-training on face images of multiple patients by using, as supervised information, information indicating a body fluid volume of each of the plurality of patients when the face images of the plurality of patients are captured;

processing of further performing transfer learning on multiple face images of one specific patient after the pre-training, and constructing a trained model; and processing of estimating, by inputting a face image of the one specific patient to the trained model, a body fluid volume of the one specific patient at a point in time at which the face image of the one specific patient is captured.

While the disclosure has been particularly shown and described with reference to embodiments thereof, the disclosure is not limited to these embodiments. It will be understood by those of ordinary skill in the art that various changes in form and details may be made therein without departing from the spirit and scope of the present disclosure as defined by the claims.

What is claimed is:

1. A body fluid volume estimation device comprising:

at least one memory configured to store instructions; and at least one processor configured to execute the instructions to:

perform pre-training on face images of multiple patients by using, as supervised information, information indicating a body fluid volume of each of multiple patients when the face images of multiple patients are captured;

perform transfer learning on multiple face images of one specific patient after the pre-training, and construct a trained model; and estimate, by inputting a face image of the one specific patient to the trained model, a body fluid volume of the one specific patient at a point in time at which the face image of the one specific patient is captured, wherein the at least one processor is further configured to execute the instructions to perform pre-training by weight-aware supervised momentum contrast (Weight-SupMoCo).

2. The body fluid volume estimation device according to claim 1, wherein the information indicating the body fluid volume of each multiple patients when the face images of the multiple patients are captured includes information indicating presence or absence of a swelling in the face image of each of the multiple patients, and information indicating weight of each of the multiple patients, and wherein the at least one processor is further configured to execute the instructions to estimate presence or absence of a swelling and predicts weight of the one specific patient at a point in time at which the face image of the one specific patient is captured by inputting the face image of the one specific patient to the trained model.

3. The body fluid volume estimation device according to claim 2, wherein the at least one processor is further configured to execute the instructions to:

detect, based on an prediction result of the presence or absence of the swelling of the one specific patient, whether the body fluid volume of the one specific patient is changed from a preset standard body fluid volume of the one specific patient; and acquire, from an estimation result of the weight, a difference in the body fluid volume of the one specific patient from the standard body fluid volume.

4. The body fluid volume estimation device according to claim 2, wherein the information indicating the presence or absence of the swelling in the face image of each of the multiple patients is label information representing the presence or absence of the swelling, and wherein the at least one processor is further configured to execute the instructions to perform pre-training in such a way that feature values of face images having the same label information representing the presence or absence of the swelling are brought closer as the information indicating the weight is more similar.

5. The body fluid volume estimation device according to claim 2, wherein the multiple patients and the one specific patient are a patient who receives dialysis, and wherein weight of each of the multiple patients and the one specific patient after dialysis associated with a case without a swelling has a value acquired by subtracting a body fluid volume removed by dialysis from weight of each of the multiple patients and the one specific patient before dialysis associated with a case with a swelling.

6. The body fluid volume estimation device according to claim 2, wherein the multiple patients and the one specific patient are a patient who receives dialysis, and wherein weight of each of the multiple patients and the one specific patient before dialysis associated with a case with a swelling has a value acquired by adding a body fluid volume removed by dialysis to weight of each of the multiple patients and the one specific patient after dialysis associated with a case without a swelling.

7. The body fluid volume estimation device according to claim 2, wherein the multiple patients and the one specific patient are a patient who receives dialysis, and wherein weight of each of the multiple patients and the one specific patient before dialysis associated with a case with a swelling has a value acquired by adding a body fluid volume removed by dialysis to preset standard weight of each of the multiple patients and the one specific patient.

8. The body fluid volume estimation device according to claim 1, wherein the at least one memory is further configured to store the face images of the multiple patients to be used for pre-training, the information indicating the body fluid volume of the multiple patients when the face images of the multiple patients are captured, and the multiple face images of the one specific patient to be used for the transfer learning, wherein the at least one processor is further configured to execute the instructions to:

read, from the at least one memory, the face images of the multiple patients and information indicating the body fluid volume when the face images of the multiple patients are captured, and performs pre-training;

read, from the at least one memory, the multiple face images of the one specific patient; and perform transfer learning.

9. The body fluid volume estimation device according to claim 1, further comprising an image capturing device, wherein the face image of the one specific patient is captured by the image capturing device.

10. A body fluid volume estimation method performed by at least one processor of a body fluid volume estimation device including the at least one processor and at least one memory configured to store instructions, the processor executing the instructions to:

perform pre-training on face images of multiple patients by using, as supervised information, information indicating a body fluid volume of each of the multiple patients when the face images of the multiple patients are captured;

perform transfer learning on multiple face images of one specific patient after the pretraining, and constructing a trained model; and estimate, by inputting a face image of the one specific patient to the trained model, a body fluid volume of the one specific patient at a point in time at which the face image of the one specific patient is captured, wherein the at least one processor is further configured to execute the instructions to perform pre-training by weight-aware supervised momentum contrast (Weight-SupMoCo).

11. A non-transitory computer-readable medium storing a program causing at least one processor of a body fluid volume estimation device including the at least one processor and at least one memory configured to store instructions to execute the instructions to:

perform pre-training on face images of multiple patients by using, as supervised information, information indicating a body fluid volume of each of the multiple patients when the face images of the multiple patients are captured;

perform transfer learning on multiple face images of one specific patient after the pretraining, and constructing a trained model; and estimate by inputting a face image of the one specific patient to the trained model, a body fluid volume of the one specific patient at a point in time at which the face image of the one specific patient is captured, wherein the at least one processor is further configured to execute the instructions to perform pre-training by weight-aware supervised momentum contrast (Weight-SupMoCo).

* * * * *